United States Patent [19]

Brown et al.

[11] Patent Number: 5,316,922

[45] Date of Patent: May 31, 1994

[54] METHOD FOR INDENTIFYING AND EXPRESSING PROTEINS THAT RECOGNIZE AND ADHERE TO SPECIFIC PROBES

[75] Inventors: Stanley Brown; Donald Court, both of Frederick, Md.

[73] Assignee: The United States of America as represented by Department of Health and Human Services

[21] Appl. No.: 869,912

[22] Filed: Apr. 15, 1992

[51] Int. Cl.[5] .................. G01N 33/53; C12Q 1/02; C12N 15/10

[52] U.S. Cl. .................. 435/69.7; 435/7.37; 435/7.8; 435/7.32; 935/79

[58] Field of Search .................. 435/7.32, 7.37, 69.7; 530/333, 413; 935/9.79, 10

[56] References Cited

U.S. PATENT DOCUMENTS 4,784,952  11/1988  Ludwig et al. .

FOREIGN PATENT DOCUMENTS 2035384    8/1991  Canada .
WO90/02809 3/1990  PCT Int'l Appl. .
91/05858   4/1991  PCT Int'l Appl. .

OTHER PUBLICATIONS

A. Charbit et al., Gene 70:181-189 1988.
Devlin, J. J., et al., "Random Peptide Libraries: A Source of Specific Protein Binding Molecules", Science 249:404-406 (1990).
Clackson, T., et al., "Making Antibody Fragments Using Phage Display Libraries", Nature 352:624-628 (1991).
Cwirla, S. E., et al., "Peptides on Phage: A Vast Library of Peptides for Identifying Ligands", Proc. Natl. Acad. Sci. USA 87:6378-6382 (1990).
Scott, J. K. and Smith, G. P., "Searching for Peptide Ligands with an Epitope Library", Science 249:386-390 (1990).

Primary Examiner—Robert J. Hill, Jr.
Assistant Examiner—Lorraine M. Spector
Attorney, Agent, or Firm—Townsend and Townsend, Khourie and Crew

[57] ABSTRACT

This invention provides for improved means to produce binding specific proteins using concatamers of semi-randomly generated oligonucleotides inserted into genes encoding the external domains of bacterial outer membrane proteins. The genes are induced to express and the bacteria are then screened for the ability to bind to predetermined compositions. Those clones carrying the desired binding protein are isolated, cultured and the protein purified. Increased avidity of the binding specific proteins are achieved by reisolating the oligonucleotides which conferred binding affinity and mixing them with new semi-randomly generated oligonucleotides to generate a population enriched for oligonucleotides that had previously conferred to bacteria the desired binding affinity. The enriched population of oligonucleotides is then religated to the gene encoding the external domain of the bacterial protein, the gene is inserted into a bacterial cell and the cells analyzed for increased avidity for the predetermined composition.

12 Claims, 2 Drawing Sheets

METHOD FOR INDENTIFYING AND EXPRESSING PROTEINS THAT RECOGNIZE AND ADHERE TO SPECIFIC PROBES

BACKGROUND OF THE INVENTION

This invention provides for improved means to produce binding specific proteins using concatamers of semi-randomly generated oligonucleotides inserted into genes encoding the external domains of bacterial outer membrane proteins. The genes are induced to express and the bacteria are then screened for the ability to bind to predetermined compositions. Those clones carrying the desired binding protein are isolated, cultured and the protein purified. Increased avidity of the binding specific proteins are achieved by reisolating the oligonucleotides which conferred binding affinity and mixing them with new semi-randomly generated oligonucleotides to generate a population enriched for oligonucleotides that had previously conferred to bacteria the desired binding affinity. The enriched population of oligonucleotides is then religated to the gene encoding the external domain of the bacterial protein, the gene is inserted into a bacterial cell and the cells analyzed for increased avidity for the predetermined composition.

Semi-random oligonucleotides have been previously identified as a means to obtain binding proteins specific for a predetermined composition. Typically such work involves recombinantly inserting short oligonucleotides into the binding sites of antibodies and laborious screening procedures. CA patent application Ser. No. 2,035,384. Other work involves assaying a phage library having random inserts. WO 91/050058 describes a cell-free method for screening random peptides for binding specificity.

SUMMARY OF THE INVENTION

This invention provides for a method for generating a binding protein able to bind to a predetermined composition. The method comprises the following steps: (a) generating a first pool of semi-random, double-stranded polynucleotides of between 4 and 100 triplet codons having no UGA or UAA codons and bearing flanking complementary sticky ends which form a restriction site when joined; (b) inserting said polynucleotides into a portion of a gene encoding an external domain of a bacterial outer membrane protein to obtain a library of modified genes containing semi-random inserts; (c) transforming a gram negative bacterial cell with the library of modified genes wherein the modified genes are operably linked to a promoter which functions in said cell; (d) culturing said bacteria under conditions permitting expression and transport of proteins encoded from the modified genes including the binding protein wherein said transport is to the outer membrane; and, (e) selecting and isolating bacteria with the ability to bind to the predetermined composition as a result of the expression of the binding protein.

Variations of this method include the use of bacteria which comprise a UAG suppressor phenotype. Preferred bacteria are E. coli and Salmonella typhimurium. The mutated protein can be an endogenous bacterial outer membrane protein and are preferably selected from the group of genes consisting of: porins and transport proteins.

The predetermined composition may be selected from the group consisting of: metal oxides, proteins, carbohydrates, vitamins, plastic polymers and vitamins and even more specifically can be selected from the group consisting of: iron oxide, biotin, and the human Mos protein.

A further adaption of the above-described method includes the additional steps of (f) isolating the semi-random insert of the modified gene encoding the bacterial cell surface protein from the bacteria of step e; (g) treating the insert with a restriction enzyme which cleaves the restriction sites formed through the complementary binding of the sticky ends to form a second pool of polynucleotides; (h) mixing the second pool with additional semi-random polynucleotides of between 4 and 100 triplet codons having no UGA or UAA codons and having sticky ends complementary to those of the second pool so as to yield a third pool of semi-random polynucleotides; (i) inserting the third pool of semi-random polynucleotides into the portion of the gene encoding the external domain of the bacterial outer membrane protein; and, (j) repeating steps c-e.

This invention further provides for bacteria produced by the methods described above.

The invention further provides for a bacterial cell surface protein able to bind to a predetermined composition not naturally binding to said protein and wherein said protein is produced according to the methods described herein.

Finally the invention provides for a method for generating random polypeptides in bacteria comprising: (a) generating semi-random oligonucleotides of between 4 and 100 triplet codons each lacking adenine in the third position; (b) making concatamers of the semi-random oligonucleotides; (c) inserting the concatamers into an expression cassette; (d) transforming the expression cassette into a host cell competent to express said cassette; and, (e) culturing the host cell under condition permitting the express of said cassette. It is preferred that the concatamers are between 8 and 200 codons and the host cell be a bacterial cell.

DESCRIPTION OF THE DRAWINGS

FIG. 1 describes the relative positions of the ClaI, XhoI, and SmaI restriction sites and the PCR primer sites in cloning vector pSB1649. The arrow indicates the direction of transcription of lamB. Various numbers of 11 codon oligonucleotides are shown inserted into the XhoI site of the vector.

FIG. 2 is a photograph of the products of the PCR amplification. The amplified products were electrophoresed in 6% polyacrylamide gel in TBE and stained with ethidium bromide. The positions of the PCR products of the vector with no insert (0) and the vector bearing 6 oligonucleotides inserted are indicated to the left of the gel. lane 1: starting population, lane 2: 4 cycles of induction with IPTG transfer to adhesion buffer and return to growth medium, lanes 3, 4, and 5: 3, 4, and 5 cycles of enrichment with iron oxide. lane 6: pSB1972, lane M:φX174 HaeIII digest.

DETAILED DESCRIPTION

Figure 1:
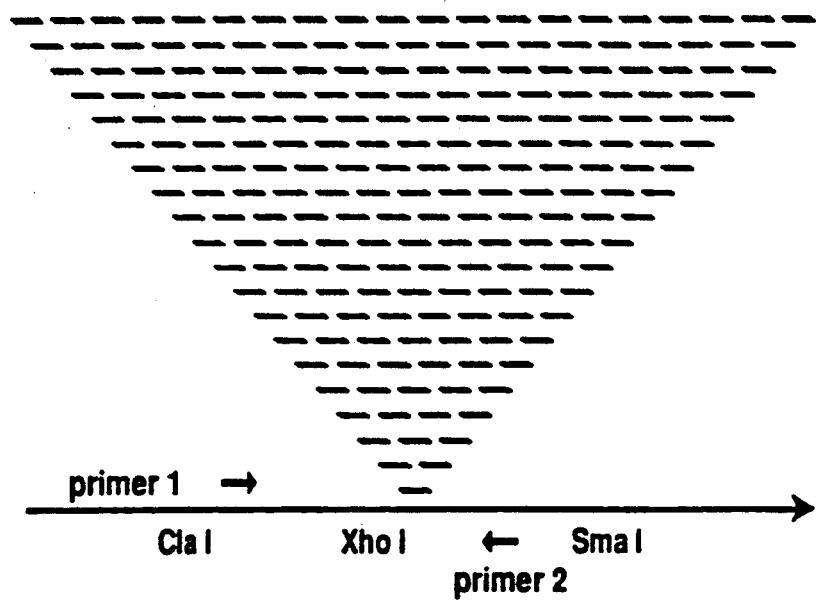
FIG. 1.

The invention disclosed herein makes use of the field of biochemistry and molecular biology to produce adhesion mutants in bacteria. Where routine technology is being described, no attempt is made to describe what is already known. Unless otherwise specified the genetic and biochemical manipulations described herein are as detailed in Sambrook, J. et al. *Molecular Cloning, a laboratory manual* (Cold Spring Harbor Laboratory Press, Cold Spring Harbor, N.Y., ed. 2, 1989) [hereinafter "Sambrook"] or according to the manufacturer's suggested protocol.

The adhesion mutants are the result of modified outer bacterial proteins. In nature, these proteins are expressed and transported to the outer cell membrane of bacteria where their external domain is in contact with the environment and thus available for binding interactions with specified or predetermined compositions. These proteins are quite varied and include both endogenous proteins and phage-related proteins.

Outer membrane bacterial proteins include naturally-occurring proteins such as transport proteins encoded by the following genes: tsx, btu, and lamB; porins such as encoded by the following genes: ompC, ompD, ompF and phoE; and fimbriae such as encoded by fim. Phage induced outer membrane bacterial proteins would include that encoded by the lom gene of lambda phage.

This invention is not limited to the use of endogenous bacterial proteins. One could readily transform a bacteria with a heterologous gene encoding one of the above proteins.

The external domain of an outer membrane bacterial protein is identified using routine technology, EMBO J. 5:3029–3037, 1986. In brief, linker scanning is used to identify sites in the protein which can accept small inserts and retain function. Then a known epitope is inserted at the site of the linker and mapped using antibodies.

It is not necessary that the modified gene remain functional. It is necessary that the modification not significantly affect the ability of the cell to transport the protein beyond the inner membrane nor its ability to integrate properly into the outer membrane. It is also preferred that the protein be present on the bacterial surface in a sufficient quantity that detection via adhesion is possible.

Once the bacterial protein has been selected and the region of modification identified, the gene must be inserted into a suitable expression plasmid. Expression of heterologous genes are well-known. The promoter can either be the native promoter or a more preferably a highly efficient and inducible heterologous promoter such as the Lac promoter.

The gene is preferably modified to permit ready insertion of the semi-random insert. This is typically done by use of a restriction enzyme site which is unique in the gene sequence. If a convenient site is present it may be used. Otherwise, a unique restriction site can be engineered in situ [Sambrook].

Having obtained the desired gene having a unique restriction site in the external domain, one must obtain the semi-random inserts. The semi-random inserts are a random population of concatamers of semi-random, double-stranded polynucleotides. The semi-random polynucleotides have complementary sticky ends which permit concatamerization. The semi-random polynucleotides are generated using a single stranded synthetic template of the design X—(NNB)$_n$—X wherein X represents a nucleotide sequence recognized by the same restriction enzyme which cleaves the unique restriction site in the above-described plasmid containing the outer membrane bacterial protein and wherein (NNB) represent a population of semi-random triplet codons. The triplet codons are semi-random because during synthesis, adenine is not permitted in the third position of any codon. Both ends of the oligonucleotides are the same and can be inserted into the gene in two orientations, i.e., NNB or VNN where V represents A, G, or C, B represents T, G, or C and N represents A, G, C, or T. This permits desirable variability while still excluding nonsense codons. More specifically, this precludes the possibility of nonsense codons UAA or UGA from being present. The n can be between 4 and 100. It is preferred that be between 8 and 20, to facilitate control over the size of the semi-random insert and to permit efficient shuffling. Concatameric inserts can be greater than 200 codons but are typically less than 100 codons.

The semi-random template is synthesized using conventional technology and can be obtained from commercial laboratories offering custom oligonucleotides. Such laboratories include the Midland Certified Reagent Co., 1500 Murray St.; Midland, Tex.

The template is used to generate a population of semi-random polynucleotides having complementary sticky ends. The polynucleotides are generated using an appropriate DNA polymerase and the synthetic templates. Appropriate polymerases would preferably include such proof-reading polymerases such as the Vent TM polymerase (New England Biolabs) or the Klenow fragment of Pol I. Where a primer is needed, short oligonucleotides complementary to the 5' end of the template may be used. Conditions for polymerase activity are well-known and optimum conditions will vary for each enzyme.

The semi-random polynucleotides are then isolated and purified using conventional techniques. It is preferred that the polynucleotides are isolated from the polymerase by gel electrophoresis. The polynucleotides are then purified from the gel and saved.

The semi-random polynucleotides are then permitted to form concatamers. The array of concatamers typically being random with the number of semi-random polynucleotide members (n) being from 1 to greater than 20. Concatamerization typically takes place in a general ligation buffer [Sambrook] supplemented with high salts (e.g., NaCl, 0.1M) to ensure retention of the duplex structure. The concatamerization may optionally take place in the presence of the plasmid containing the outer membrane bacterial protein where that plasmid has been previously linearized by restriction enzyme which recognizes the unique site in the external domain and the sites formed when the flanking sticky ends of the semi-random polynucleotides are joined to their complementary sequences.

The concatamers are then ligated to each other and to the expression plasmid using a ligase such as T4 ligase. The result of this ligation is a mixed population of plasmids carrying the outer membrane protein gene modified with varying numbers of semi-random polynucleotides arranged as concatamers each concatamer linked to each other by sequences defining the same enzyme restriction site.

To facilitate selection of bacteria transformed with the plasmid, the plasmid should comprise, in addition to a suitable origin of replication, a suitable selectable marker. Suitable selectable markers are well known and include genes encoding antibiotic resistance, colored products and genes conferring the ability to survive on nutrient deficient media.

The mixed population of plasmids is then transformed into a suitable bacterial strain. Suitable strains are any gram negative bacteria which can transcribe the expression cassette and transport the translated product across its inner membrane and into the outer membrane. Suitable strains include *E. coli, Salmonella typhimurium,* Bacillus strains, *Agrobacterium tumefaciens* and other commonly used host cells. Transformation means are generally known and described in Sambrook.

Although not required, the efficiency of the system will be increased if the bacterial strain has the ability to recognize the normally nonsense codon UAG as a translatable codon. Such mutations are well studied and are described in the literature as UAG suppressors. Such suppressors include supE, and supF.

After transformation the bacteria are then cultured in a suitable growth medium. The choice of growth media is non-critical. It should include sufficient nutrients to support logarithmic growth of the bacteria.

After culturing, the bacteria are optionally assayed to ensure that the plasmids are representative of a vast array of the semi-random inserts. The most convenient means to assay the plasmids is to culture a random sample and isolate the plasmid containing the recombinantly modified gene. The semi-random insert is then amplified using PCR. More specifically, PCR primers complementary to the upstream and downstream sequences of the gene encoding the outer membrane protein are used to amplify the internal sequences representing the semi-random insert. The amplified product is then sized by gel electrophoresis to ensure that the desired array of concatamers is present.

To ensure that the inserts comprise random arrays of different semi-random polynucleotides, one can optionally sequence the nucleotides comprising the inserts. This step is optional.

Having determined that the bacterial population comprise the desired array of semi-random inserts in the nucleic acid encoding the external domain of the outer membrane protein, the bacteria are then exposed or contacted with the predetermined composition and selection pressure used to enrich the population for those clones able to bind selectively to the predetermined composition.

The predetermined composition can be any material to which a protein can bind. Predetermined compositions can be as varied as the number of antigens to which an immune system can recognize. Predetermined compositions include without limitation: proteins, lipoproteins, lipids, carbohydrates, glycoproteins, polymers, inorganic compounds, organic compounds, pesticides, viruses, metals, metal oxides, ceramics and plastics.

The selection procedure to enrich the bacterial population for adhesion mutants involves binding bacteria to the predetermined composition, removing the composition-bound bacteria and permitting the bound bacteria to grow free of the predetermined composition. This process is then repeated until the bound population is reflective of those mutations which are binding with specificity to the predetermined composition.

The predetermined composition can be suspended in the adhesion buffer or bound to a second material (e.g. a solid support of cellulose, plastic or sepharose) which is readily removed from the medium such as a dipstick, filter paper disk or paramagnetic beads which are removed by magnetic force.

The adhesion buffer is a physiologically compatible buffer having suitable osmolarity and pH to sustain bacteria (i.e., M63 salts). With *E. coli*, one should either use fim$^-$ strains or add D-mannose to inhibit nonspecific adhesion.

It is expected that with each replication of the selection procedure the population of bacteria will become enriched with bacteria having the capacity to bind to the predetermined composition. This enriched population may or may not be a homogeneous population. Therefore insert size and sequence analysis should be used in the latter phases of enrichment to ensure identification of the most avidly binding of the population. If the enriched population is a mixed population, single cell culturing techniques are used to isolate the various clones. Subsequent identification of the most avid clones is achieved using routine titration experiments.

Once a suitable bacterial clone has been identified, the insert can be used as a basis for enrichment of a second series of selections to isolate bacteria with even greater binding affinity. This second series of selection steps involves a shuffling technique which takes advantage of the restriction sites separating the semi-random polynucleotides forming the concatameric insert of the plasmid encoding the binding specific protein.

The plasmid encoding the binding protein from the first selection steps is isolated from a culture of the host bacteria. The insert is then amplified in situ using PCR. The amplified product is then digested to completion using the restriction enzyme recognizing the sites flanking each of the semi-random polynucleotides, the digestion products are then isolated using gel electrophoresis and saved.

The saved semi-random polynucleotides are then mixed with a second set of double stranded, semi-random polynucleotides having sticky ends complementary to the sticky ends of the saved polynucleotides. Preferably, the proportion of saved polynucleotides to second set of polynucleotides is between 1:5 to 1:20. This generates a third population of semi-random polynucleotides which is enriched with semi-random polynucleotides which encoded for a protein insert having the desired binding affinity. The third population is then permitted to form concatamers and ligated to the identical site of the expression plasmid used previously.

The same series of steps are carried out to select for bacterial adhesion mutants with an increased binding affinity for the predetermined composition.

This invention has multiple uses, the proteins generated can be used to form smart glues which bind to predetermined compositions, to make protective coatings which preferentially bind to select sites such as corroding or rusting pipes or as proteins which can substitute for the various uses that immunoglobulins are presently used.

EXAMPLES

The following examples are provided by way of illustration and are not meant to limit the claims. Those of skill will readily recognize numerous non-critical parameters which could be varied to achieve substantially similar results.

EXAMPLE 1

Engineering an Iron Oxide Binding Mutant of lamB in *E. coli*

The following bacterial strains were used: S1755: F$^-$lacI$^Q$ ΔmalB101 end A hsdR17 supE44 thi1 relA1 gyrA96, S1918: as S1755 but fim, S1995: same as S1755 but lamB, S1964: as S1918 but ara::Tn10 mini-tet.

To generate a pool of single-stranded, semi-random polynucleotides a template oligonucleotide of the following sequence was used:
(Seq. ID No. 5.) 5' GGACGCCTCGAG(VNN)9CTCGAGAGCAACAAT 3'. The template was synthesized by the phosphoramidite method. Where V represents A, G, or C and N represents A, G, C, or T. To generate double- stranded, semi-random polynucleotides, primer oligonucleotides of the sequence (Seq. ID. No.5) , 5' ATTGTTGCTCTCGAG 3' which is complementary to the downstream constant region, were annealed and extended with Klenow fragment of DNA polymerase [Sambrook]. The product was chromatographed on Sephadex G25 and digested with XhoI at 30° C. The internal 33 bp fragment was purified by electrophoresis in 16% polyacrylamide gel in TBE at 4° C. [Sambrook].

The purified double-stranded, semi-random 33 base pair fragments were then ligated to XhoI digested pSB1649. Plasmid pSB1649 bears a single XhoI site in a portion of the lamB gene that encodes the external domain of the lambda receptor. The lamB gene is expressed from the easily regulated lac promoter. Plasmid pSB1649 is a derivative of the lamB expression vector pAC1, developed by Hofnung and coworkers (*Mol. Gen. Genet.* 205:339, 1986). To prepare pSB1649, codons representing amino acids 155 and 156 of the mature lambda-receptor were converted in the lamB gene of pAC1 to an XhoI restriction site. This was achieved by using synthetic oligonucleotides.

Figure 2:
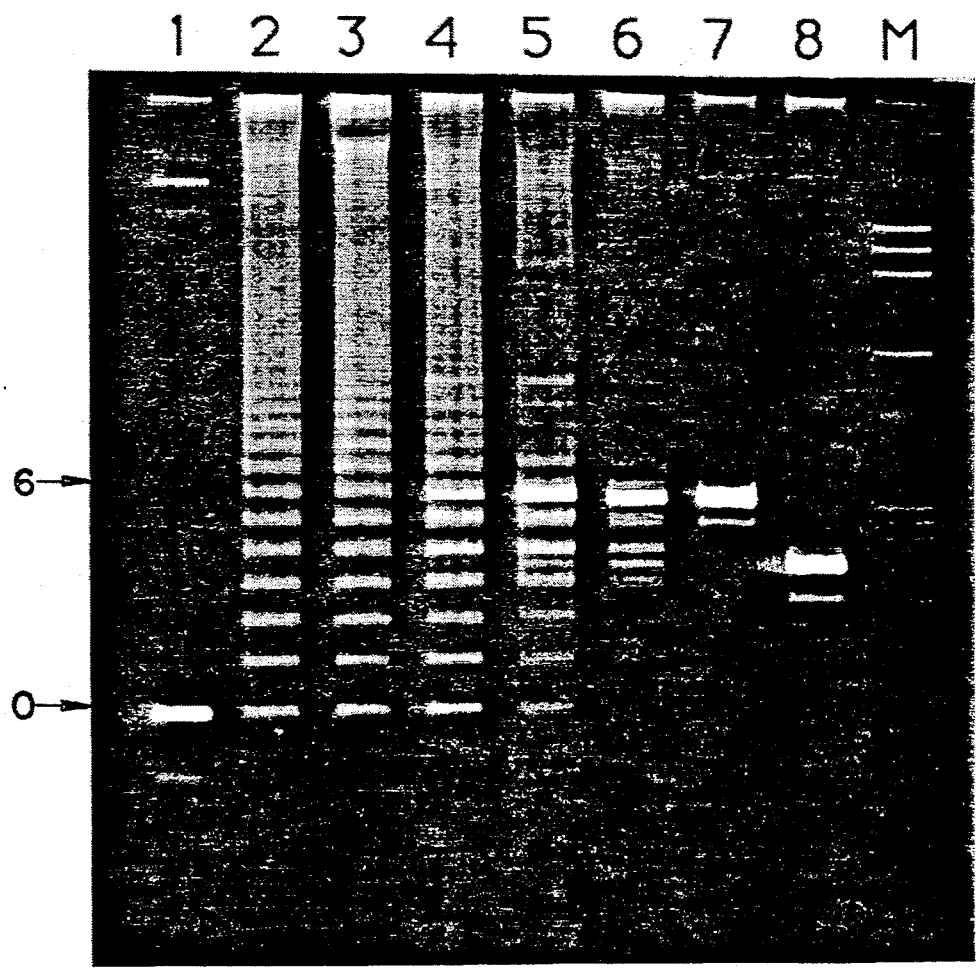
FIG. 2.

The ligation product was ethanol precipitated, chromatographed on Sepharose 4B, and transformed into S1755 using the rubidium chloride protocol #3 described by D. Hanahan in DNA Cloning, D. M. Glover, Ed. (IRL Press, Oxford, 1985, pp:109-135. A population of $2.2 \times 10^6$ clones was cultured. The size distribution of the insert population was monitored by PCR amplification. (FIG. 1). More specifically, CsCl-ethidium bromide purified plasmid DNA was digested with DraI because DraI recognition sites are not expected to appear in the nearly random oligonucleotide inserts. The digests were PCR amplified 15 cycles with Vent TM polymerase (New England Biolabs) using PCR primers (Seq. ID. No 1) 5' ACATCGATGTTGGCTTCGGT 3', and 5'ATCTGCGCTAAACGCACATCG3'. Products of the PCR amplification were electrophoresed in 6% polyacrylamide gel in TBE (Sambrook) and stained with ethidium bromide. In the starting population, the number of concatamers of 33 mer oligonucleotides was distributed uniformly from 0 to greater than 20 semi-random polynucleotides. The various bands generated had equal intensity after ethidium bromide staining. Each size class of between 0 and 20 contained 100,000 or more different clones (FIG. 2).

To induce expression of the modified lamB genes of pSB1649 in strain S1755, the bacteria were cultured in YT broth as described by J. H. Miller, *Experiments in molecular genetics*, (Cold Spring Harbor Laboratory, Cold Spring Harbor, N.Y., 1972). Log-phase cultures of the bacterial population were established at 37° C. in YT broth supplemented with 200 µg/ml ampicillin. Isopropyl-β-D-thiogalactopyranoside [IPTG] was added to a final concentration of 2 mM and incubation continued at 37° C. for 15 minutes.

To identify transformants able to bind to the surface of iron oxide particles, iron oxide was purchased as a dark brown aqueous suspension (cat# 4200B) from Advanced Magnetics. Expression of the engineered lambda-receptors was induced as described above and the bacteria recovered by centrifugation and resuspended with adhesion buffer (1 mM D-mannose in M63 salts). The bacterial suspension was mixed with a suspension of 200 µg/ml of iron oxide in adhesion buffer and the mixture incubated at room temperature for 10 minutes.

The iron oxide with the adhering bacteria were recovered by placing the culture tube next to a magnet. Following the magnetic separation, the liquid and non-adhering bacteria were removed by aspiration and the culture tube removed from the vicinity of the magnet. The iron oxide-bound cells were resuspended with M63 salts, and spread on YT-ampicillin agar. Dilutions of the suspension were also spread to monitor population sizes. After overnight incubation of the agar plates at 37° C., colonies appearing on the surface were pooled, exponentially growing cultures were established, and the induction and enrichment procedure repeated.

In the absence of iron oxide, four cycles of induction, transfer to adhesion buffer, and plating did not appreciably change the distribution of the insert population as measured by the combination PCR and electrophoresis analysis described above. In contrast, enrichment in the presence of iron oxide did appreciably change the distribution of the insert population. Clones bearing an insert of 6 oligonucleotides become highly represented in the enriched population. (FIG. 2) 10 individual survivors of the fifth cycle of enrichment were purified, and the plasmid DNA prepared. Restriction analysis of the plasmids indicated that 7 of the 10 examined bore ClaI - SmaI fragments approximately 200 bp larger than did the vector pSB1649, representing 6 oligonucleotides inserted into the XhoI site.

The sequence constraints of the oligonucleotides generates a 54% probability that an insert of 6 oligonucleotides would contain at least one Bsp1286 site. All 7 plasmids bearing the 6 semi-random polynucleotides had acquired a single Bsp1286 site in the same location (the 3' end of the fifth oligonucleotide inserted) indicating they are likely to be siblings. One of these plasmids, pSB1972 was characterized further. In an independent enrichment from the same starting population, 5 of 6 survivors harbored plasmids bearing an insert of 6 oligonucleotides, all 5 of which contained a single Bsp1286 site in the same location as in pSB1972. One member of the second set was sequenced and found to bear the same sequence as pSB1972. Thus the enrichment strategy employed here is probably capable of recovering the strongest binder from the starting pool.

The method of Andrews and Lin (J. Bacteriol. 128: 510, 1976) was used to determine that the ability to adhere to iron oxide is directed by the plasmid-borne lamB gene. The results of this test are shown in Table 1. In this test, both the vector, pSB1649, and the recovered clone, pSB1972, are transformed into a pair of strains that vary in their ability to ferment arabinose. The transformants are then mixed and the composition of the mixture monitored by spreading on arabinose indicator agar. The results in Table 1 indicate the ability to be enriched by adhering to iron oxide is dependent on the plasmid pSB1972, independently of which host bears pSB1972. The observation of a greater than 40 fold enrichment per cycle predicts a more rapid enrichment of pSB1972 bearing bacteria than observed in the initial population when monitored by PCR. The enrichment rate is probably reduced by competition with other iron oxide adhering bacteria that are enriched by the process.

TABLE 1

| Enrichment | % pSB1972 in starting population | % pSB1972 in enriched population | fold enrichment |
|---|---|---|---|
| Experiment 1: | | | |
| M63 | 0.20% | 0.71% | 3.5 |
| Iron Oxide | 0.13% | 5.7% | 45. |
| Experiment 2: | | | |
| M63 | 0.42% | 0.18% | |
| NH2-Biomag | 0.42% | 1.1% | 2.7 |
| Iron Oxide | 0.42% | 18.% | 43. |

In experiment 1, pSB1972 (lamB gene bearing insert) was in an Ara- host, and pSB1649 (lamB+) was in an Ara+ host. In experiment 2, the hosts for the two plasmids were reversed, pSB1972 in Ara+ and pSB1649 in Ara-. In both experiments, log phase cultures of the two transformants were diluted, mixed, and grown as a mixed culture prior to IPTG induction.

The ability of pSB1972 bearing bacteria to associate with iron oxide was monitored using phase contrast microscopy. In this experiment, transformants harboring pSB1972 were mixed with iron oxide and examined visually. The formation of visible aggregates was dependent on the presence of both bacteria carrying pSB1972 and iron oxide. Neither transformants harboring the vector, pSB1649, induced with IPTG, nor transformants harboring pSB1972 when not induced with IPTG aggregate in the presence of iron oxide under these conditions.

The ability of pSB1972 to confer specific adherence to metal oxides was also examined by phase contrast microscopy. In this experiment, the following metal oxides were purchased from Aldrich: $Fe_2O_3$ cat# 20,351-3, $Fe_3O_4$ cat# 31,006-9, $Cr_2O_3$ cat# 20,306-8, $Co_3O_4$ cat# 20,311-4. It was determined that SB1972, but not pSB1649 permits adherence to $Fe_2O_3$. The weak adherence to $Fe_3O_4$ may be intrinsic to $Fe_3O_4$ or due to a small amount of $Fe_2O_3$ present on the surface of the $Fe_3O_4$. The absence of adherence to $Cr_2O_3$ and $Co_3O_4$ indicated the specificity of binding by the pSB1972 lamB product. This specificity may be a reflection of the tightness of binding to $Fe_2O_3$.

The nucleotide sequence of the pSB1972 insert and surrounding region of lamB is presented in Sequence Listing ID. No. 1. It can be seen that no nonsense codons appear in the insert. Examination of the sequence of the insert shows the third and sixth oligonucleotides are inserted in the "no A in the third position" orientation, and the second, fourth, and fifth oligonucleotides are inserted in the "no T in the first position" orientation.

To further increase the avidity of the lamB mutant, the insert is removed from p1972 using XhoI. The inserts are purified and digested with XhoI to regenerate the original six 33 mer oligonucleotides. These are then mixed with A 1:10 amount of semi-random 33 mer double-stranded oligonucleotides and joined with T4 ligase to form concatamers. The concatamers are then combined with pSB1649 to form a second random plasmid population enriched with those oligonucleotides conferring iron oxide binding specificity to the lambda receptor. The plasmids are then inserted into S1918 to form a second library which is then screened for the ability to bind to iron oxide.

The resulting clone with plasmid pSB2071 demonstrated increased avidity over pSB1972.

EXAMPLE 2

Engineering a $Co_3O_4$ Binding Mutant of lamB in *E. coli*

Following the procedures outlined in example 1 but substituting $Co_3O_4$ for iron oxide, one can obtain a $Co_3O_4$ binding mutant of lamB. Differential sedimentation is substituted for retrieval by magnetic force.

EXAMPLE 3

Engineering a Biotin Binding Mutant of lamB in *E. coli*

Following the procedures outlined in example 1 but substituting biotin-bound-sephadex for iron oxide and substituting a biotinylated plastic dipstick for magnetic separation, one can obtain a biotin binding mutant of lamB.

EXAMPLE 4

Engineering an Iron Oxide Binding Mutant of lamB in *Salmonella typhimurium*

Following the procedures outlined in example 1 but substituting *Salmonella typhimurium*, strain LT-1, one can obtain an iron oxide binding mutant of lamB in *Salmonella typhimurium*.

EXAMPLE 5

Engineering an Iron Oxide Binding Mutant of phoE in *E. coli*

Following the procedures outlined in example 1 but substituting the porin gene phoE for lamB, one can engineer an iron oxide binding mutant of phoE in *E. coli*.

EXAMPLE 6

Engineering an Iron Oxide Binding Mutant of lamB in *Agrobacterium tumefaciens*

Following the procedures outlined in example 1 but substituting *A. tumefaciens* for *E. coli*, one can engineer an iron oxide binding mutant of *A. tumefaciens*. For a description of typical genetic techniques for engineering different genera of bacteria with the lamB gene, with examples for *A. tumefaciens*, including preferred media, the reader is referred to U.S. Pat. No. 4,784,952 which is incorporated by reference herein.

What is claimed:

1. A method for generating a binding protein able to bind to a predetermined composition which comprises:
   (a) generating a first pool of semi-random, double-stranded polynucleotides of between 4 and 100 triplet codons having no UGA or UAA codons in either orientation and bearing flanking complementary sticky ends which form a restriction site when joined;
   (b) randomly ligating said polynucleotides to form a pool of concatamers of different lengths;
   (c) inserting said concatamers into a portion of a gene encoding an external domain of a bacterial outer membrane protein to obtain a library of modified genes containing semi-random inserts, where the inserts vary in length and base composition;
   (d) transforming a gram negative bacterial cell with the library of modified genes wherein the modified genes are operably linked to a promoter which functions in said cell;
   (e) culturing said bacteria under conditions permitting expression and transport of proteins encoded from the modified genes including the binding protein wherein said transport is to the outer membrane; and,
   (f) selecting and isolating bacteria with the ability to bind to the predetermined composition as a result of the expression of the binding protein.
   (g) isolating the semi-random insert of the modified gene encoding the bacterial cell surface protein from the bacteria of step f;
   (h) treating the inert with a restriction enzyme which cleaves the restriction sites formed through the complementary binding of the sticky ends to form a second pool of semi-random double stranded polynucleotides;
   (i) mixing the second pool with additional semi-random double stranded polynucleotides of between 4 and 100 triplet codons having no UGA or UAA codons and having sticky ends complementary to those of the second pool so as to yield a third pool of semi-random polynucleotides;
   (j) repeating steps b–g.

2. A method of claim 1 wherein the bacterial cell of step d comprises a UAG suppressor phenotype.

3. A method of claim of claim 2 wherein the UAG suppressor selected from the group consisting of supE and supF.

4. A method of claim 1 wherein the bacterial cell is selected from the group consisting of *E. coli* and *Salmonella typhimurium*.

5. A method of claim 1 wherein the bacterial outer membrane protein is an endogenous protein.

6. A method of claim 1 wherein the predetermined composition is selected from the group consisting of: metal oxides, proteins, carbohydrates, plastic polymers and vitamins.

7. A method of claim 1 wherein the predetermined composition is selected from the group consisting of: iron oxide, biotin, and the human Mos protein.

8. A method of claim 1 wherein the outer membrane gene is selected from the group of genes consisting of: porins and transport proteins.

9. A method of claim 8 wherein the gene is selected from the group consisting of: ompC, ompD, ompF, phoE, tsx, btu, and lamB.

10. A method of claim 1 wherein the gene is the lamB gene.

11. A method of claim 1 wherein the selecting step involves the binding of the bacteria to magnetic beads coated with the predetermined composition.

12. A method of claim 1 further comprising the purification of the bacterial cell surface protein having the ability to bind to the predetermined composition.

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:

(A) LENGTH: 369 base pairs
(B) TYPE: nucleic acid
(C) STRANDEDNESS: single
(D) TOPOLOGY: linear (ii) MOLECULE TYPE: DNA (genomic)

(ix) FEATURE:
    (A) NAME/KEY: CDS
    (B) LOCATION: 1..369
    (D) OTHER INFORMATION: /note="Iron oxide binding mutant
        of the lambda receptor of E. coli"

(ix) FEATURE:
    (A) NAME/KEY: miscfeature
    (B) LOCATION: 11..30
    (D) OTHER INFORMATION: /note="ClaI / primer 1"

(ix) FEATURE:
    (A) NAME/KEY: miscfeature
    (B) LOCATION: 333..353
    (D) OTHER INFORMATION: /note="primer 2"

(xi) SEQUENCE DESCRIPTION: SEQ ID NO:1:

```
GGT CTG GAA AAC ATC GAT GTT GGC TTC GGT AAA CTC TCT CTG GCA GCA    48
Gly Leu Glu Asn Ile Asp Val Gly Phe Gly Lys Leu Ser Leu Ala Ala
 1               5                  10                  15

ACC CGC TCC TCT GAA GCT GGT GGT TCT TCC TCT CTC GAG CGC CGC ACT    96
Thr Arg Ser Ser Glu Ala Gly Gly Ser Ser Ser Leu Glu Arg Arg Thr
                 20                  25                  30

GTT AAG CAT CAC GTG AAC CTC GAG GAC ACA ATA GCA ATC AAG GAA GAC   144
Val Lys His His Val Asn Leu Glu Asp Thr Ile Ala Ile Lys Glu Asp
             35                  40                  45

ATC CTC GAG ATC ACT GCT CTG GCT CGC TCC ACT CTT CTC GAG GAA CGT   192
Ile Leu Glu Ile Thr Ala Leu Ala Arg Ser Thr Leu Leu Glu Glu Arg
         50                  55                  60

ATC AAG CCC ACA CGC CTT GCA CTC GAG ATC ACC GCA CCA AAA CGC CTG   240
Ile Lys Pro Thr Arg Leu Ala Leu Glu Ile Thr Ala Pro Lys Arg Leu
 65                  70                  75                  80

CCC GTG CTC GAG AGT CCT CTT GAG TTG TCC CGG CAG ATT CTC GAG AGC   288
Pro Val Leu Glu Ser Pro Leu Glu Leu Ser Arg Gln Ile Leu Glu Ser
                 85                  90                  95

AAC AAT ATT TAT GAC TAT ACC AAC GAA ACC GCG AAC GAC GTT TTC GAT   336
Asn Asn Ile Tyr Asp Tyr Thr Asn Glu Thr Ala Asn Asp Val Phe Asp
                100                 105                 110

GTG CGT TTA GCG CAG ATG GAA ATC AAC CCG GGC                       369
Val Arg Leu Ala Gln Met Glu Ile Asn Pro Gly
            115                 120
```

(2) INFORMATION FOR SEQ ID NO:2:

(i) SEQUENCE CHARACTERISTICS:
        (A) LENGTH: 123 amino acids
        (B) TYPE: amino acid
        (D) TOPOLOGY: linear (ii) MOLECULE TYPE: protein (xi) SEQUENCE DESCRIPTION: SEQ ID NO:2:

```
Gly Leu Glu Asn Ile Asp Val Gly Phe Gly Lys Leu Ser Leu Ala Ala
 1               5                  10                  15

Thr Arg Ser Ser Glu Ala Gly Gly Ser Ser Ser Leu Glu Arg Arg Thr
                 20                  25                  30

Val Lys His His Val Asn Leu Glu Asp Thr Ile Ala Ile Lys Glu Asp
             35                  40                  45

Ile Leu Glu Ile Thr Ala Leu Ala Arg Ser Thr Leu Leu Glu Glu Arg
         50                  55                  60

Ile Lys Pro Thr Arg Leu Ala Leu Glu Ile Thr Ala Pro Lys Arg Leu
```

|       |       |       |       |       |       |       |       |       |       |       |       |       |       |       |       |
|-------|-------|-------|-------|-------|-------|-------|-------|-------|-------|-------|-------|-------|-------|-------|-------|
| 65    |       |       |       | 70    |       |       |       | 75    |       |       |       | 80    |       |       |       |

Pro Val Leu Glu Ser Pro Leu Glu Leu Ser Arg Gln Ile Leu Glu Ser
               85                     90                    95

Asn Asn Ile Tyr Asp Tyr Thr Asn Glu Thr Ala Asn Asp Val Phe Asp
            100                    105                  110

Val Arg Leu Ala Gln Met Glu Ile Asn Pro Gly
        115                  120

( 2 ) INFORMATION FOR SEQ ID NO:3:

( i ) SEQUENCE CHARACTERISTICS:
        ( A ) LENGTH: 165 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..165

( x i ) SEQUENCE DESCRIPTION: SEQ ID NO:3:

GAG CAG CCC AAC AGC CAT GGT AGC GCC TGT CTC GAG CGC CGC ACT GTT    48
Glu Gln Pro Asn Ser His Gly Ser Ala Cys Leu Glu Arg Arg Thr Val
 1                  5                 10               15

AAG CAT CAC GTG AAC CTC GAG CTG AGA ATG AAG AAC CCC ACA AAA AAT    96
Lys His His Val Asn Leu Glu Leu Arg Met Lys Asn Pro Thr Lys Asn
               20                  25               30

CTC GAG GGA AGC AAG ATG GAG GAC AAC GGA ATC CTC GAG ATC AAG GAA  144
Leu Glu Gly Ser Lys Met Glu Asp Asn Gly Ile Leu Glu Ile Lys Glu
        35                    40               45

GGT GCA GTG GCA GCC AAG CTC                                          165
Gly Ala Val Ala Ala Lys Leu
        50                    55

( 2 ) INFORMATION FOR SEQ ID NO:4:

( i ) SEQUENCE CHARACTERISTICS:
        ( A ) LENGTH: 55 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

Glu Gln Pro Asn Ser His Gly Ser Ala Cys Leu Glu Arg Arg Thr Val
 1                  5                 10               15

Lys His His Val Asn Leu Glu Leu Arg Met Lys Asn Pro Thr Lys Asn
               20                  25               30

Leu Glu Gly Ser Lys Met Glu Asp Asn Gly Ile Leu Glu Ile Lys Glu
        35                    40               45

Gly Ala Val Ala Ala Lys Leu
        50                    55

( 2 ) INFORMATION FOR SEQ ID NO:5:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( i i ) MOLECULE TYPE: DNA (template oligonucleotide)

( i x ) FEATURE:
        ( A ) NAME/KEY: miscfeature
        ( B ) LOCATION: 40...54

-continued ( D ) OTHER INFORMATION: /note="polymerase primer"

( x i ) SEQUENCE DESCRIPTION: SEQ ID NO:5:

GCACGCCTCG AGVNNVNNVN NVNNVNNVNN VNNVNNVNNC TCGAGAGCAA CAAT  54